(12) United States Patent
Angermann et al.

(10) Patent No.: US 11,017,526 B2
(45) Date of Patent: May 25, 2021

(54) METHOD AND APPARATUS FOR REAL-TIME DETECTION OF POLYPS IN OPTICAL COLONOSCOPY

(71) Applicants: CENTRE NATIONAL DE LA RECHERCHE SCIENTIFIQUE—CNRS—, Paris (FR); UNIVERSITE DE CERGY PONTOISE, Cergy Pontoise (FR); ECOLE NAT SUP ELECTRONIQUE APPLICATION, Cergy Pontoise (FR); ASSISTANCE PUBLIQUE HOPITAUX DE PARIS, Paris (FR); SORBONNE UNIVERSITE, Paris (FR)

(72) Inventors: Quentin Angermann, Cergy (FR); Xavier Dray, Paris (FR); Olivier Romain, Montgeron (FR); Aymeric Histace, Conflans Sainte-Honorine (FR)

(73) Assignees: CENTRE NATIONAL DE LA RECHERCHE SCIENTIFIQUE, Paris (FR); UNIVERSITE DE CERGY PONTOISE, Cergy Pontoise (FR); ECOLE NAT SUP ELECTRONIQUE APPLICATION, Cergy Pontoise (FR); ASSISTANCE PUBLIQUE HOPITAUX DE PARIS, Paris (FR); SORBONNE UNIVERSITE, Paris (FR)

(*) Notice: Subject to any disclaimer, the term of this patent is extended or adjusted under 35 U.S.C. 154(b) by 211 days.

(21) Appl. No.: 16/314,817
(22) PCT Filed: Jun. 19, 2017
(86) PCT No.: PCT/EP2017/064972
  § 371 (c)(1),
  (2) Date: Jan. 2, 2019
(87) PCT Pub. No.: WO2018/007139
  PCT Pub. Date: Jan. 11, 2018

(65) Prior Publication Data
  US 2019/0311474 A1    Oct. 10, 2019

(30) Foreign Application Priority Data

Jul. 4, 2016 (EP) .................................. 16177835

(51) Int. Cl.
  *G06T 7/00* (2017.01)
  *G16H 30/40* (2018.01)
  (Continued)

(52) U.S. Cl.
  CPC .......... *G06T 7/0012* (2013.01); *G06K 9/6257* (2013.01); *G06K 9/6262* (2013.01);
  (Continued)

(58) Field of Classification Search
  CPC ............ G06T 2207/10068; G06T 2207/30032
  See application file for complete search history.

(56) References Cited

U.S. PATENT DOCUMENTS 7,177,454 B2 * 2/2007 McLaren ............... G01N 1/312
                                                345/604
7,190,818 B2 * 3/2007 Ellis .................... G01N 15/1475
                                                382/128
(Continued)

FOREIGN PATENT DOCUMENTS

WO    2015/031641 A1    3/2015
WO    WO-2015031641 A1 *  3/2015 ............... G06T 7/13

OTHER PUBLICATIONS

Y. Wang, "Polyp-Alert: Near real-time feedback during colonoscopy", computer methods and p rograms in biomedicine 120 (2015) 164-179. (Year: 2015).*

(Continued)

*Primary Examiner* — Gandhi Thirugnanam
(74) *Attorney, Agent, or Firm* — BakerHostetler

(57) ABSTRACT

A method for performing real-time detection and displaying of polyps in optical colonoscopy, includes a) acquiring and
(Continued)

displaying a plurality of real-time images within colon regions to a video stream frame rate, each real-time image comprising a plurality of color channels; b) selecting one single color channel per real-time image for obtaining single color pixels; c) scanning the single color pixels across each the real-time image with a sliding sub-window; d) for each position of the sliding sub-window, extracting a plurality of single color pixels local features of the real-time image; e) passing the extracted single color pixels local features of the real-time image through a classifier to determine if a polyp is present within the sliding sub-window; f) real-time framing on display of colon regions corresponding to positions of the sliding sub-window wherein polyps are detected. A system for carrying out such a method is also provided.

22 Claims, 2 Drawing Sheets

(51) Int. Cl.
G06K 9/62 (2006.01)
G06T 7/73 (2017.01)
G06T 7/70 (2017.01)

(52) U.S. Cl.
CPC .............. G06K 9/6292 (2013.01); G06T 7/70 (2017.01); G06T 7/73 (2017.01); G06T 7/75 (2017.01); G16H 30/40 (2018.01); G06T 2207/10016 (2013.01); G06T 2207/10024 (2013.01); G06T 2207/10048 (2013.01); G06T 2207/10068 (2013.01); G06T 2207/20064 (2013.01); G06T 2207/20081 (2013.01); G06T 2207/30032 (2013.01)

(56) References Cited

U.S. PATENT DOCUMENTS

| | | | | |
|---|---|---|---|---|
| 8,724,866 B2* | 5/2014 | Wu | .................... | G06K 9/4638 382/128 |
| 8,923,585 B1* | 12/2014 | Peleg | .................... | G06T 7/0012 382/128 |
| 9,092,691 B1* | 7/2015 | Beaumont | ............ | G06T 7/0014 |
| 2002/0097320 A1* | 7/2002 | Zalis | ........................ | G06T 7/12 348/65 |
| 2006/0079761 A1* | 4/2006 | Tu | ........................ | G06K 9/6257 600/425 |
| 2006/0239552 A1* | 10/2006 | Tu | ........................ | G06K 9/4638 382/173 |
| 2007/0078335 A1* | 4/2007 | Horn | ..................... | A61B 1/041 600/425 |
| 2008/0147577 A1* | 6/2008 | Bi | ........................ | G06K 9/6257 706/12 |
| 2008/0194946 A1* | 8/2008 | Summers | ............ | A61B 5/7267 600/425 |
| 2009/0097728 A1* | 4/2009 | Lee | ........................ | G06T 7/155 382/131 |
| 2009/0252389 A1* | 10/2009 | Yamaguchi | .......... | A61B 5/0059 382/128 |
| 2010/0061609 A1* | 3/2010 | Shinagawa | ........... | G06T 7/0012 382/131 |
| 2011/0188706 A1* | 8/2011 | Zhou | ........................ | G06K 9/00 382/103 |
| 2012/0316421 A1* | 12/2012 | Kumar | ................... | A61B 1/041 600/407 |
| 2013/0109915 A1* | 5/2013 | Krupnik | ................ | G06F 3/0482 600/109 |
| 2014/0051586 A1* | 2/2014 | Pino | ....................... | C07K 16/18 506/2 |
| 2015/0043799 A1* | 2/2015 | Zhan | .................... | G06K 9/3233 382/131 |
| 2015/0065850 A1* | 3/2015 | Jia | ...................... | A61B 1/00009 600/408 |
| 2016/0078625 A1* | 3/2016 | Tajbakhsh | ............ | G06K 9/4642 382/128 |
| 2017/0046835 A1* | 2/2017 | Tajbakhsh | ................. | G06T 7/73 |
| 2018/0225820 A1* | 8/2018 | Liang | .................... | G16H 30/20 |
| 2019/0311474 A1* | 10/2019 | Angermann | ......... | G06K 9/6292 |
| 2020/0268364 A1* | 8/2020 | Watanabe | .......... | A61B 1/00045 |
| 2020/0395117 A1* | 12/2020 | Schnorr | ................ | G16H 30/20 |

OTHER PUBLICATIONS

Silva, et al., "Towards real-time in situ polyp detection in WCE images using a boosting-based approach", Conf Proc IEEE Eng Med Biol Soc, pp. 5711-5714, Jul. 3, 2013.

Cheng, et al., "Colorectal Polyps Detection Using Texture Features and Support Vector Machine", Advances in Mass Data Analysis of Images and Signals in Medicine, Biotechnology, Chemistry and Food Industry, pp. 62-72, Jul. 14, 2008.

Sun, et al., "Lesion detection of gastroscopic images based on cost-sensitive boosting", 2011 IEEE International Workshop on Machine Learning for Signal Processing, pp. 1-6, Sep. 18, 2011.

Bernal et al., "Towards Automatic Polyp Detection with a Polyp Appearance Model", Pattern Recognition, vol. 45, No. 9, p. 3166-3182, 2012.

* cited by examiner

METHOD AND APPARATUS FOR REAL-TIME DETECTION OF POLYPS IN OPTICAL COLONOSCOPY

CROSS-REFERENCE TO RELATED APPLICATIONS

This application is a National Stage of International patent application PCT/EP2017/064972, filed on Jun. 19, 2017, which claims priority to European Patent Application No. EP 16177835.2, filed on Jul. 4, 2016, the disclosures of which are incorporated by reference in their entirety.

The present invention relates to the field of features recognition in imaging and more specifically to the real-time detection of polyps within regions of the colon using machine learning techniques.

s Polyps are an abnormal growth of the tissue that may be benign or malignant. Early stage detection of polyps, independently of the risks they may represent is an important step towards both cancer prevention and fatality decrease. Colorectal cancer (CRC) is one of the main causes of death by cancer in the world, with an estimated incidence of 1.370.600 new cases in the world in 2012 and with a fatal outcome in 50% of cases. Today, up to 26% of polyps can be missed during optical colonoscopy sessions. This relatively high figure is partly due to circumstances in which images are acquired within colon regions, but also by the size of the polyps. A certain number of parameters are contributing to such high miss rate and they are as follows:
  the time of the day the detection occurs, for example during the morning or the afternoon,
  the skills of the clinician performing the detection,
  how well the colon is prepared, for instance low-fiber food should be ingested days prior examination for optimal image rendition, Furthermore, polyp detection is also plagued by some of the current methodologies necessitating high computational power and lengthy post detection analysis of acquired images. Last but not least, as of today, analysis of the acquired images has to be performed offline. Offline meaning the delay between instants of detection and analysis of the result is spanning from seconds to hours. This has repercussions on both the detection process and the result itself.

There are considerable numbers of techniques to detect polyps. In order to evaluate these techniques and compare them, some quantitative and qualitative metrics have been introduced. The metrics relate firstly to the capability of the technique to detect polyps and secondly how genuine these detections are. These metrics are as follows:
  True Positive (TP): A true positive detection is the result when a polyp is properly detected by the system.
  False Positive (FP): A false positive detection is the result when a polyp is found positive while it was not.
  False Negative (FN): A false negative detection is the result when a polyp is said negative while it was positive.
  Recall: it represents the percentage of true detections provided by the system.
  Precision: also known as Sensitivity or True Positive Rate (TPR), is used to indicate the number of polyps that have been detected out of the total number of polyps.
  F2 Score: it combines Precision and Recall giving more weight to recall. This is used to make a balance between the number of false detection and the number of missed polyps. A high F2 score shows a good tradeoff between Precision and Recall.

A few systems and methodologies are currently competing in order to ensure more reliable detection systems or techniques while sustaining a certain degree of consistency on whether a polyp has been detected or not. Two major paths are currently under investigation, the software and the hardware based approaches. Even though both approaches have their strengths and weaknesses, so far none of them succeeded to clearly prevail on the other one.

In the computer-assisted approach, the hardware aspect of the entire apparatus is less of a concern. In prior art, "Towards Automatic Polyp Detection with a Polyp Appearance Model", J. Bernal et al., Pattern Recognition, 2012, vol. 45, no 9, p. 3166-3182, the software approach was used in order to detect polyps. The method is based on colonoscopy images where focus is on regions description as a function of depths of valleys. A three stage detection algorithm performed on captured images allowed a modeling of the appearance of a polyp. The method is using a region descriptor based depth of valleys, so called SA-DOVA (Sector Accumulation-Depth Of Valleys). The resulting algorithm is divided into three steps, region segmentation, region description and region classification with binary decision on SA-DOVA maxima. This method takes on average up to 19 seconds to process a single image. The method is to a certain extent limited, as there is a pre-selection of regions of the image where polyps are likely to be found. Other regions are not further processed, this could lead to miss some of the polyps.

The document WO2015/031641 is also a software based system and method for automatic polyp detection. The method teaches steps to perform automatic boundary detection of polyps and is parameterized to detect edges of polyps within previously acquired images. The detection is such as it is shape-independent and captures color variation across the boundary of polyps with Haar feature extraction. Haar features are defined as the intensity difference of the sum of pixels of areas inside neighboring rectangles for example. Haar features indicate the presence or not of certain characteristics in the image; such as for example a change of texture or color of neighboring rectangles where calculations are performed. Haar features tend to require substantial amount of computational power. To train the classifier, the method uses random forest, which is a regression algorithm built with 30 decision trees based on pixels features previously detected by a Canny's algorithm.

Even though the detection rate of the method is among state of the art results, it does appear to take a certain time to process an image. This is most likely due to all the computational power required to compute all the different algorithms.

The hardware approach may lean towards state of the art miniaturized devices that may be for example swallowed, such as a capsule endoscopy camera. Such miniaturized devices can be the size of a vitamin capsule embedded for example with a camera, wireless capabilities and the necessary sub-system to process images. The patient may then be equipped with a recording device capable of storing images sent from the capsule. From the time capsules begin their journey through the intestine until they get expelled out naturally of the body, they can take up to 50000 images. These images will be processed manually, which is a tedious task and increases chances of missing polyps. The document US2015/0065850 is a method of detecting polyps through images acquired with a wireless capsule endoscopy. The principle of the method is to prune a plurality of images acquired from the device to only keep those which are likely to contain polyps. Features of images containing polyp candidates are extracted before a regression step is applied to determine if the candidate is effectively a polyp. In this method, Local Binary Patterns (LBPs) are used to extract features of images. Specificities of LBPs are such as a targeted pixel is assigned a single bit weight according to its relative intensity regarding a pixel comprised in circular set of neighboring pixels. If the targeted pixel intensity is greater than its neighbor, then its assigned weight is 0 and 1 if otherwise. Assignation of binary weights is repeated for all the pixels of the circular set of neighboring pixels and until a binary word is formed. LBP is an effective texture based means of extracting local features of an image, yet it requires very little computational power. Even though the method takes as low as 0.83 second to process a single image, its true positive detection rate of 64.8% is not on par with its speed.

However, none of these documents provide a solution to implement a real-time detection method or system with comparatively low computational power—e.g. the one provided by a day-to-day use computer—while sustaining satisfactory true positive detection rate.

The present invention is introducing a fast, therefore real-time compliant detection method of polyps including means to acknowledge such detection. The method is software based and can be performed with a computational power similar to the one provided by a laptop. One of the aspect of the method is the extraction of local features, e.g. using LBPs, in order to take advantage of their fast and little computational power requirements. Another aspect is the use of a machine learning technique to train a classifier using a boosting algorithm, in order to identify polyps and learn from its mistakes. Once trained, the arbitrary named strong classifier is capable in tens of milliseconds to identify polyps features. Because of the assistance provided by the classifier in such method, skills of the clinician performing the detection are not as decisive as it may be in other techniques.

The method consists of first acquiring images in real-time within the colon region at a video stream frame rate. Then, only one channel color is selected for each individual image in order to reduce the computational time. The next step consist of scanning across the entire area of each image with a sliding sub-windows to extract for each position of the sliding sub-windows the local features of the colon region of interest. Next, these local features are passed through a classifier in order to determine whether a polyp is present or not for the scanned position of the sliding sub-windows. Finally, if a polyp is detected there will be a real-time framing on a display of the region where such polyp is detected.

This method has first of all the advantage of being non-invasive. This is becoming a more and more decisive criterion for both patients and medical staff during the choice of a technique to be used in colonoscopy. Because the detection method is fast, its result is rendered in real-time. Even though it is fast, it still yields high rate of true positive detection. Using the same database, some techniques of the art return similar figure in terms of true positive detection rate, but are several order of magnitude slower.

An object of the invention is then a method of performing real-time detection and displaying of polyps in optical colonoscopy, characterised in that it comprises the steps of:
a) acquiring and displaying a plurality of real-time images (109) within colon regions to a video stream frame rate, each real-time image comprising a plurality of color channels;
b) selecting one single color channel per real-time image for obtaining single color pixels;
c) scanning the single color pixels across each said real-time image with a sliding sub-window;
d) for each position of said sliding sub-window, extracting a plurality of single color pixels local features of the real-time image;
e) passing the extracted single color pixels local features of the real-time image through a classifier to determine if a polyp is present within the sliding sub-window;
f) real-time framing on display of colon regions corresponding to positions of said sliding sub-window wherein polyps are detected.

A "local feature" is a numerical value, or set of values, defined by a function of a set of neighboring color pixels of the selected color channel (more precisely, of their luminance). The neighboring pixels are adjacent pixels chosen in a small area (whose exact size and shape depends on the local features considered) around a "central" pixel. For instance, a local feature may be a function of the central pixel and some or all of its first neighbors only (i.e. pixels in direct contact with the central pixel), or of the central pixel and some or all of its first and second neighbors only (second neighbors are pixels in direct contact with at list one first neighbor of the central pixel, except the central pixel itself and other first neighbors thereof), or of the central pixel and some or all of its first, second and third neighbors only (third neighbors are pixels in direct contact with at list one second neighbors of the central pixel, except first neighbors and other second neighbors). Advantageously, a number A>1 of local features are computed for each pixel of the sliding window. The overall number of local features computed for a n×m pixel sliding window is then A·m·n. A typical value for "A" is 10 or more. Considering a 60×60 pixel sliding windows, the number of local features computed for each position of the window may be of the order of 36.000.

Local features shall not be confused with global features. A global feature is a mean of a feature of all the single color pixels of the image, or of the sliding window, or of a "patch", i.e. a set of the sliding window including more than a central pixel and its neighbors as defined above.

According to particular embodiments of the invention:
Step c) may comprise scanning without polyp boundaries detection.
The method may further comprise selecting a blue single color channel.
The method may comprise local features chosen from the group comprising local binary patterns and Haar-like features. However, in different embodiments, other local feature can be used, such as Histogram of Gradients, or SIFT descriptors.
The method may comprise associating local feature to a respective classifier, called weak classifier, the classifier used in step e) of the method comprising a sum of at least one hundred weak classifiers.
The method may further comprise a classifier based on a boosting algorithm, such as Cascade Adaboost. A boosting algorithm comprises several "stages" (e.g. 10) and local features are recomputed for each stage. Considering a 10-stage boosting algorithm, A=10 and a 60×60 pixel sliding window, the total number of local features to be computed for each position of the sliding window is as high as 360.000. However, local features are defined by very simple functions of a small number of pixels, therefore their computation is extremely fast, making the inventive method suitable to real-time implementation despite their great number.

The method may further comprise a preliminary step of creating said classifier by active learning.

Said active learning is carried out using a learning database comprising datasets of training images, wherein said training images include ground truth images of known polyps, the active learning comprising the steps of:

s1) selecting a fraction of dataset images for training purposes and another fraction of dataset images for testing purposes;

s2) extracting said fraction of dataset images for training purposes from said learning database, and selecting one single color channel from each of said images;

s3) computing a first classifier based on a boosting algorithm on said fraction of dataset of images for training purposes, and testing it on said fraction of dataset images for testing purposes;

s4) identifying false detection cases of polyps by said classifier during said testing;

s5) using said false detection cases of polyps to create a new classifier, based on a Cascade boosting algorithm;

steps s3) to s5) being repeated a plurality of times to create a final classifier, wherein the classifier used in step e) of the method is said final classifier.

The method may comprise repeating steps s3) to s5) exactly three times.

The method may comprise the step of scanning realized p times with p being odd and greater than one, each time with one different size of the sliding sub-windows, and wherein in the step e) a majority vote is performed to determine if a polyp is present.

Said real-time images are acquired at a minimum frame rate of 24 images per second.

Another object of the invention is a system for real-time image detection and displaying of polyps comprising an input port (104) for receiving a video stream, an image processor (105) for processing images from said video stream and an output port (106) for outputting processed images (109), characterised in that the image processor is configured for:

a) acquiring and displaying a plurality of real-time images within colon regions to a video stream frame rate, each real-time image comprising a plurality of color channels;

b) selecting one single color channel per real-time image for obtaining single color pixels, each real-time image comprising a plurality of color channels;

c) scanning the single color pixels across each said real-time image with a sliding sub-window;

d) for each position of said sliding sub-window, extracting a plurality of single color pixels local features of the real-time image;

e) passing the extracted single color pixels local features of the real-time image through a classifier to determine if a polyp is present within the sliding sub-windows;

f) real-time framing (108) on display (102) of colon regions corresponding to positions of said sliding sub-window wherein polyps are detected.

According to particular embodiments of the invention:

An optical colonoscopy apparatus may comprise an optical colonoscopy probe (103) connected to an input port of said system.

A more complete understanding of the present disclosure thereof may be acquired by referring to the following description taken in conjunction with the accompanying drawings wherein.

Figure 1:
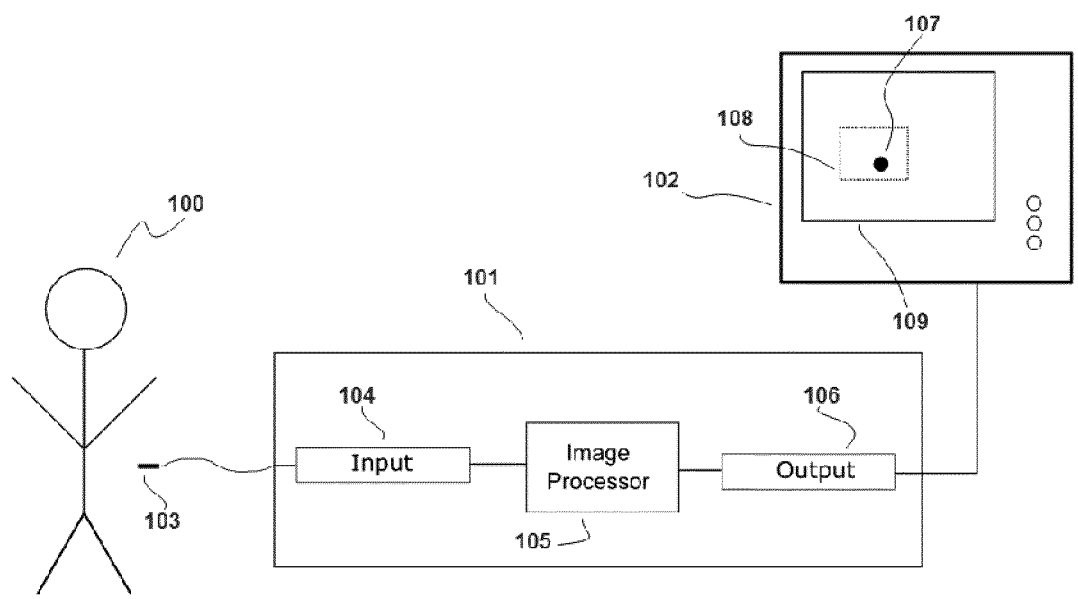
FIG. 1 is a representation of the apparatus for real-time detection of polyps.

While the present invention is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

FIG. 1 is a generic schematic representation of the apparatus used for detecting polyps. The patient 100 on whom the optical colonoscopy is performed is illustrated on FIG. 1. A probe 103 is inserted in the colon of the patient to acquire a plurality of images in real-time, forming a video stream (video-colonoscopy); the invention may also apply to other optical colonoscopy technology, such as wireless capsule endoscopy. Said probe is an optical fiber like camera capable of acquiring said plurality of images in real-time. The probe is connected to the input 104 of the polyps real-time detection system 101. Said input of the real-time detection system receives a video stream of images provided by said probe. Video stream is sent to the image processor 105 configured for real-time processing of said video stream. The image processor comprises a DSP (Digital Signal Processing) pertinently programmed to execute the steps of detecting polyps within said plurality of real-time images. Once processed, said video stream by means of the detection system output 106, is sent to the monitor 102 for real-time display of said plurality of acquired images. The monitor displays in real-time the detection of a polyp 107 wherein the framing 108 is the acknowledgement of such detection.

The video may be a High Definition (HD, 1440×1080 pixels) or a Standard Definition (SD, 720×480 pixels) video.

Figure 2:
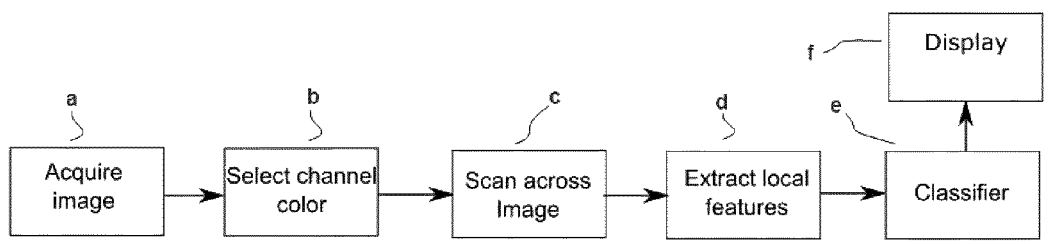
FIG. 2 is a flow diagram representing the process of real-time detection of polyps.

In FIG. 2 there is an illustration of the steps of the method for the real-time detection and display of polyps in optical colonoscopy. The method described herein is as follows:

Step a consists in acquiring and displaying a plurality of real-time images from colon regions of the patient. Said plurality of real-time images is in a video stream frame rate with each individual image comprising a plurality of channel colors. In one embodiment of the present invention, said video stream is defined to a frame rate of at least 24 frames per second. The plurality of images are acquired by the probe 103 of FIG. 1 and simultaneously displayed by the monitor 102, also represented in FIG. 1 and performed by step f of the present method. In one embodiment of the present invention, each image of the plurality of real-time images has a dimension of 400×300 pixels.

In step b there is a selection of one single color channel among the plurality of color channels. The plurality of color channels is comprised in the full-light spectrum wherein said color channels may be selected to either be visible or non visible. For example they may be comprised in the IR (Infrared) or UV (Ultra-Violet) spectrum. In one embodiment, said single color channel is selected to be visible and comprised in the RGB (Red Green Blue) color space. Limiting the image color channel to only one color whether it is visible or not, contributes towards reducing computational complexity. To further improve detection capabilities, in one embodiment of the invention, the selected single color channel is blue. Blue color helps further improve detection by rejecting parasitic effects due to blood vessels. Other embodiments may include different color spaces and various selections of color channel.

Step c performs a scanning across each real-time image with a sliding sub-window. Scanning is performed to search for polyp candidates. Contrary to many methods or techniques, the attempted detected parameter is not based on polyp boundaries. Each real-time image is thoroughly scanned across its entire area to minimize risks of missing polyps. In one embodiment of the invention, the motion of the sub-window is performed at the step of one pixel at the time. In another embodiment the motion may be performed with larger steps. The sliding window is preferably square, with a size of a few pixels, e.g. 60×60 pixels. Other embodiments may include any geometrical shape and dimensions. The sliding sub-window motion is a background process performed by the image processor 105, it is therefore neither visible by the physician performing the detection session nor displayed on the monitor 102.

In step d, for each position taken by the sliding sub-windows a plurality of single pixel color local features of the image is extracted. Said local features are the parameters by which one may distinguish a polyp from for example granulation tissue. In one embodiment, local features are LBPs. Said LPBs are locally describing the properties of polyps. A single LBP is not sufficient to reliably characterise polyps, calculating as many as possible of LBPs is necessary for strong classification decision. In another embodiment, Haar-like features are used for region description. A Haar-like feature is an algorithm based on image intensity. It rather uses a lot of computational power in order to consider adjacent rectangular regions at specific location of a detection window. It first calculates the sum of pixel intensities in said regions and then difference between these sums. This difference is then used to characterise squared regions of an image. LBPs or Haar-like features are associated to a respective classifier, and said classifier is called weak classifier.

In step e local features pass through a classifier for determining if a polyp is present within the sliding sub-windows. The classifier decides whether the extracted features are identified to be the characteristics of polyps. Process by which said classifier is obtained is a boosting algorithm which is detailed in the description of FIG. 3. In one embodiment the boosting algorithm is Adaboost. The principle of Adaboost is the selection of weak classifiers that are moderately accurate in order to create a very accurate classification rule. The result is a linear combination of the selected weak classifiers. Hence, result derived from Adaboost training is a strong classifier corresponding to a linear sum of at least one hundred weak classifiers. More particularly, in a preferred embodiment, the classifier is obtained through a cascade boosting algorithm, such as Cascade Adaboost—see FIG. 3 steps s3-s5. Preferably an active learning step consisting in reinforcing the previously obtained strong classifier by integrating, new false positive detected areas (extracted using the strong classifier) into the learning database, and iterating again steps s3 to s5.

In step f, there is a real-time display of colon regions sensed by the clinician's probe 103. If for a position of the sliding sub-window the extracted local features are identified to present similar features to polyps, then there is real-time framing 108 on monitor 102 of the polyp 107. Real-time display occurs at a video stream frame rate, along with framing if any polyps are detected.

Figure 3:
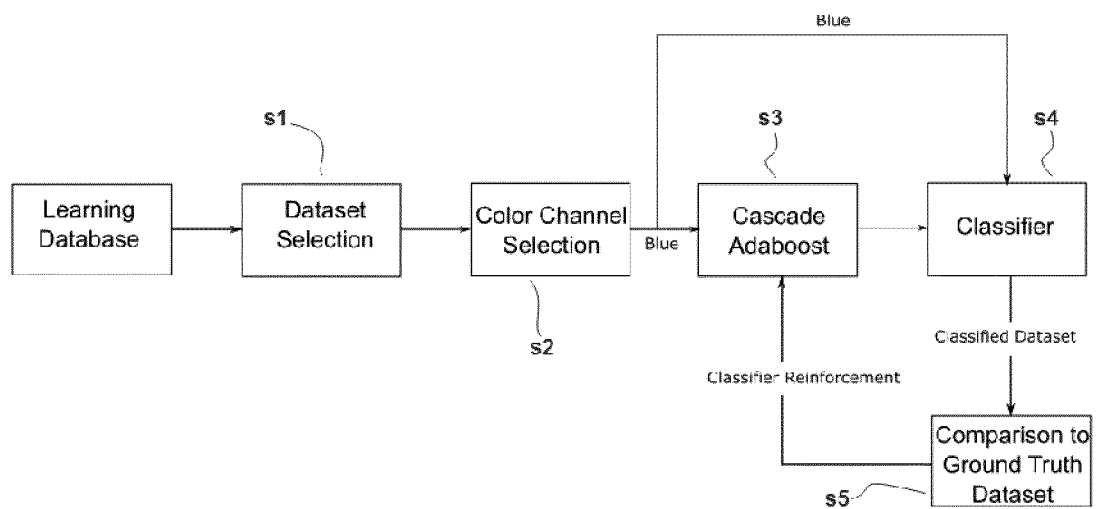
FIG. 3 is a flow diagram of the process of active learning with a boosting algorithm.

FIG. 3 is an illustration of the steps of the active learning process using the boosting algorithm allowing obtaining a strong classifier. The active learning process necessitates a learning database comprising a dataset of training images which may or not contain polyps. The method comprises the steps of:

selecting in s1 a fraction of the dataset of images contained in the learning database for either training or testing purposes. In one embodiment of the invention, the freely available database for training purposes is CVC-ClinicDB comprising 612 images with a resolution 384×288. While the testing database, also freely available, is CVC-ColonDB comprising 300 images with a resolution of 574×500.

extracting in s2 from selected fraction of dataset images for training purposes a single color channel per image. In one embodiment of the present invention, the single color channel selected per image is blue for both training and testing dataset of images.

applying in s3 a boosting algorithm such as Adaboost (in Cascade configuration) for training a first classifier using a fraction of the dataset of images. Said first classifier is a non-reinforced classifier and tested in s4 with said fraction of images dataset. On the one hand it takes said first classifier about 30 minutes to be computed with LBPs. On the other hand it takes 7 days for Haar-like features to be computed. First classifiers are both computed on a 64-bits operating system with 32 Go of allocated RAM (Random Acces Memory). Even though first classifier based on Haar-like features or LBPs computation might be time and computational power consuming, they are part of the active learning process. Once the active learning is completed, which means that the strong classifier has been reinforced (2 times in a preferred embodiment), contribution to processing time is due to the necessary time to extract local features. In the present invention this processing time is real-time compliant because extraction of local features requires low computational power.

Testing classifier in s4 to identify detection cases of polyps. Based on local features (e.g. LBP) the classifier decides whether or not polyps features are identified within the images. In one embodiment, the detection of a polyp is based on the returned value of the reinforced classifier based on LBPs. If said value is below a threshold there is no polyp detected. A polyp is detected if the value is greater than the threshold. This step is therefore classifying dataset of images according the presence or not of polyps.

identifying in s5 wrongly classified dataset of first classification step s4. Focus here is on the false detections cases of polyps. Ultimately, said false detection cases engage the reliability of first classifier decision rule. In this step the identification of false positive detections is performed through the comparison of classified images during s4 to ground truth images. Active learning boosting algorithm cornerstone consists in iterating the choice of weak classifiers using local feature signatures of ground truth images stored in a database. Said ground truth images are images which are known to effectively contain polyps or not. At this stage, miss-classified local features during first classifications are reinforced by integrating into the learning database, wrongly detected new areas as polyp by the classifier.

repeating steps s3 to s5 a plurality of times until a final classifier is obtained. Said final classifier is used in step e of FIG. 2 and is called reinforced classifier. In one embodiment of the invention, steps s3 to s5 are repeated exactly three times. The process of repeating steps s3 to s5 is used to reinforce the classifier. In one embodiment, LBP based classifier takes respectively for first, second and third reinforcement, 1, 2 and 6 hours. Classification is computed using same computer than in step s3.

Table 1 below show the computational time required for obtaining a non-reinforced classifier ($1^{st}$ line) and a $1^{st}$, $2^{nd}$ and $3^{rd}$ reinforced classifier ($2^{nd}$, $3^{rd}$, $4^{th}$ line, respectively). These classifiers were created using a same computer (a 64-bits Windows with 32 Go of RAM). For each image of the training database, the researchers identified and isolated the position of one polyp (positive example) and also isolated 5 negative examples (without polyps, negative example). To test the 'blue' component, classifiers were first trained with 550 positive examples and 3000 negative examples. Then, considering the active learning reinforcement, the three different classifiers were trained using 6000, 7500 and 8500 negative examples, respectively.

TABLE 1

| Classifier | Number of positives examples used | Number of positives examples used | Computational time |
|---|---|---|---|
| Non Reinforced Classifier | 550 | 3000 | 30 minutes |
| $1^{st}$ Reinforced Classifier | 550 | 6000 | 1 hour |
| $2^{nd}$ Reinforced Classifier | 550 | 7500 | 2 hours |
| $3^{rd}$ Reinforced Classifier | 550 | 8500 | 6 hours |

Table 2 below is a comparison of the computation results of first classification performed in step s3 according to various embodiments of the present invention, which are for different visible single color channel selections.

TABLE 2

| Local Binary Pattern Classifier | Grayscale Image | Red Channel Image | Green Channel Image | Blue Channel Image |
|---|---|---|---|---|
| True Positive Detections | 155 | 238 | 241 | 254 |
| False Positive Detections | 117 | 867 | 898 | 1067 |
| False Negative Detections | 118 | 35 | 32 | 19 |
| Recall (%) | 56.78 | 87.18 | 88.24 | 93.04 |
| Precision (%) | 56.99 | 21.54 | 21.16 | 19.23 |
| $F_2$ Score (%) | 56.82 | 54.16 | 54.01 | 52.63 |
| Average Detection Time for 1 Image (s) | 0.221 | 0.092 | 0.066 | 0.051 |

From Table 2, one can see that the single color channel blue is not only capable of detecting correctly the highest number of polyps but it is also the one necessitating the shortest time on average to process one single image.

Figure 4:
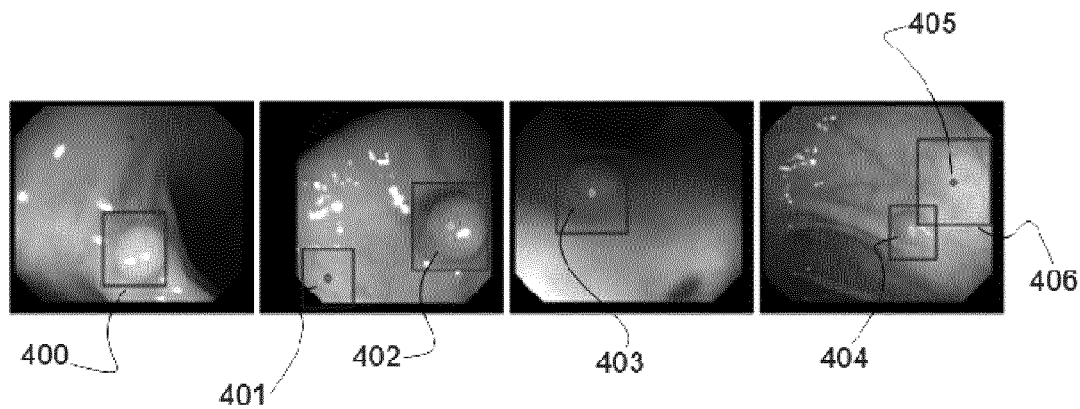
FIG. 4 is the representation of screenshots obtained during real-time detection session of polyps.

FIG. 4 is a screenshot during a session of real-time detection of polyps using the herein presented method. The method is implemented on a 64-bits operating system laptop clocked at 1.6 GHz with 4 Go of RAM. The figure illustrates true positive detections 401, 402, 403, and 404 with frames identical to 400. The dot 405 represents the center of the frame 406 acknowledging a true positive detection.

The present invention uses the same database as the previously cited prior art J. Bernal et al., therefore it is easier to compare performances of both techniques. In Table 3, best performances are overall obtained from the present invention. Results of the present invention are after three reinforcement of the classifier while using LBPs. These are shown and compared to the most up-to-date reports at the time of writing.

TABLE 3

| Authors | Performances | Database | Real-time |
|---|---|---|---|
| J. Bernal et al. | Sensitivity = 89%, F2 = 89% | CVC-ColonDB | No (19 s/image) |
| Present invention | Sensitivity = 86%, F2 = 65% | CVC-ColonDB | Yes (35 ms/image) |

Both methods have approximately the same sensitivity, 89% for prior art of J. Bernal et al. and 86% for the method of the present invention. Even though both methods are on par in terms of sensitivity their F2 score is substantially different in favor of the prior art. But the difference is even greater if one looks at the average processing time per image showing a factor of nearly 550. Prior art is almost 550 times slower than the method of the present invention. Making object of the invention real-time compliant with satisfactory detection results.

Table 4 below shows the effect of the active Learning strategy on the performances (recall, precision, F2 score, average detection time) of the inventive method. It can be seen that this strategy significantly improve the is overall performances and particularly recall and F2-score.

TABLE 4

| Classifyer using Local Binary Pattern | Without active learning | 1st Reinforced Classifier | 2nd Reinforced Classifier | 3rd Reinforced Classifier |
|---|---|---|---|---|
| Recall | 93.04% | 93.77% | 88.28% | 86.21% |
| Precision | 19.23% | 23.66% | 30.70% | 32.83% |
| F2 Score | 52.63% | 58.88% | 64.20% | 65.33% |

TABLE 4-continued

| Classifyer using Local Binary Pattern | Without active learning | 1st Reinforced Classifier | 2nd Reinforced Classifier | 3rd Reinforced Classifier |
|---|---|---|---|---|
| Average detection time for 1 image | 51 ms | 44 ms | 40 ms | 39 ms |

The implementation of the real-time detection method is not limited to a computer system. In other embodiments, one can take advantage of the low computational power requirements and use GPUs (Graphics Processing Unit), FPGAs (Field Programmable Gate Array) or even integrated computer systems like RaspberryPis to implement such method.

The AdaBoost algorithm of the present invention is developed with OpenCV. Other embodiments may include the use of different means or database to develop the algorithm.

Other embodiments may also use a different boosting algorithm such as logitboost.

In one embodiment, the scanning is performed p times with p being odd and greater than one, each time using a different size of the sliding window. The classifier is then applied to all n scans in order to decide whether a polyp is detected or not, e.g. through a majority vote (in this case, a polyp is considered present if it is detected at least p+½ times).

Figure 5:
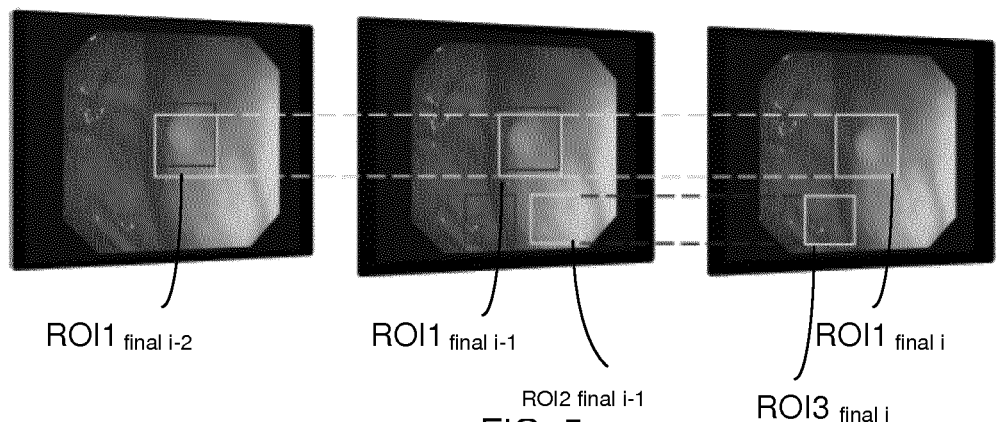
FIG. 5 illustrates spatio-temporal coherence processing according to an embodiment of the invention.

When using videos, e.g. at a typical rate of 25 frames/sec., rather than sets of still images, a significant improvement of the performances can be obtained through a "spatio-temporal coherence processing" stage. The idea is to improve the polyp detection rate and stability by combining "present" information, provided by the current frame, and "past" information, provided by previous frames showing a same region of the colon. FIG. 5 illustrates an exemplary spatio-temporal processing stage, based on a majority voting over three successive frames.

This approach is a spatial block fusion strategy to reduce the amount of candidates provided by selecting as final candidate ROI only those in which there was a higher degree of overlapping out of all the candidate boxes initially provided by the method. The spatial block fusion is applied to some successive images of a video to confirm or not the detection of a polyp by the method of the invention.

More precisely, the final sub-windows identified as polyps are defined as ROIs (Region of Interests). If multiple ROIs are located on the same regions of the image, a fusion strategy is used. This strategy consists in merging of the ROIs sufficiently overlapping (e.g. by 50% or more of their surfaces) and a final $ROI_{final}$ is generated. These ROIs within the images are defined as final $ROI_{final}$.

According to this approach, a polyp detection is confirmed at time $t_i$—corresponding to the "$i^{th}$" frame—if and only if the polyp has been detected, at a same location, in at least two among the "$(i-2)^{th}$", "$(i-1)^{th}$" and "$i^{th}$" frames. On FIG. 5, squares labeled $ROI1_{final\ i-2}$, $ROI1_{final\ i-1}$, $ROI1_{final\ i}$ identify corresponding (i.e. overlapping, e.g. by at least 70% of theirs surfaces) Regions Of Interest (ROI), containing a polyp, on three successive frames. Squares $ROI2_{final\ i-1}$ and $ROI3_{final\ i}$ correspond to unconnected ROIs in successive frames, which are not combined by the spatio-temporal coherence processing stage.

Majority voting can also be performed on more than three frames, and other spatio-temporal coherence processing method may be applied to the invention.

In other terms, the method comprises in the step e):
passing the extracted local features of single color pixels of each position of the sliding sub-window through a classifier to determine if a Region of Interest, containing a polyp, is detected, for at least one series of n successive images with a image $I_f$ displaying the Region of Interest; the image $I_f$ can be the final image of the series or not;
for each image of the series, spatial fusion of the sub-windows in which a same polyp is detected, in each successive image, for the sub-windows overlapping each other spatially on the image with at least x % of their size, to obtain $ROI_{final}$ in each successive image where there is a polyp detected; thus if there is one polyp on the image one $ROI_{final}$ is obtained on the image, and if there is two polyps two different $ROI_{final}$ are obtained on the image;
for each series of images, temporal fusion of the $ROI_{final}$ in only one $ROI_{displayed}$ by polyp detected,
for the $ROI_{final}$ of successive images overlapping each other with at least y % of their size in the referential of the images; for keeping only one $ROI_{displayed}$ by polyp detected;
the referential of the images which is common to all the images means that the mask images (having the same size) are superposed (or stacked) and the position of $ROI_{final}$ of each image is compared to the other position of the other $ROI_{final}$ of the other images of the considered series;
real-time framing on display of colon regions corresponding to position of $ROI_{displayed}$ in the final image $I_f$,
X and y being non-zero numbers.

When the image $I_f$ is the final image of the series, the method still performs completely real-time detection because the calculation realized in the method of the invention takes less than 30 ms allowing the displaying of the Region of Interest $ROI_{displayed}$ in the same time than the image which takes 40 ms to appear in a video (with 25 images/second).

In another embodiment, for instance, the image $I_f$ can be in the middle of the series of images. For instance if n=5, $I_f$ is preceded by two images and is followed by two images.

Advantageously, x is equal to or superior to 50, and y is equal to and superior to 70. These values allows to have ROI that encompasses with some precision the polyp.

Advantageously, the $ROI_{displayed}$ is calculated for some series of n successive images, n being odd and a natural integer greater than or equal to 3, and a polyp is considered present in the $ROI_{final}$ if the polyp is detected at least (n+1)/2 times in the series of the n images.

To sum up, the method takes into account three successive majority votes:
one majority vote during the step c) consisting in strengthening the classification of a sub-window using different scales of the same sub-window; for instance the polyp must have been detected on at least two scales of the same sub-window out of three; then the middle size of the polyp sub-window is stored;
one second majority vote during the step e) for spatial coherence, consisting in comparing and merging the polyp sub-windows of step c) when overlapping criteria x is filled to obtain $ROI_{final}$ for each image of the sequence; for instance a majority vote is realized on the polyp middle sub-windows for obtaining the $ROI_{final}$ of the image;
one final following majority vote during the step e) for temporal coherence, consisting in comparing $ROI_{final}$ of at least 3 successive images and merging the $ROI_{final}$ of step e) when overlapping criteria y is filled to obtain $ROI_{display}$ for each image of the sequence; for instance a majority vote is realized on the $ROI_{final}$ for obtaining the $ROI_{display}$ of the series of the images.

Table 5 below shows the results obtained using two different kind of local features for polyp detection—LBP and Haar-like features—with (STC) and without spatio-temporal coherence processing. Active learning was not used ("N0" suffix).

The following metrics were used to measure performances obtained by the inventive method on videos:
Prec: Precision;
Rec: Recall;
F1: combines Precision and Recall;
PDR: polyp detection rate;
MPT: Mean processing time per frame;
MNFP: Mean number of false positive per frame;
RT reaction time (latency between the first detection of a polyp by the algorithm and its actual appearance on the ground truth);

TABLE 5

| Methods | PDR | MPT | MNFP | Prec | Rec | F1 | RT |
|---|---|---|---|---|---|---|---|
| LBPN0 | 100% | 140 ms | 3.5 | 12.42% | 54.65% | 20.24% | 7.2 (0.3 s) |
| HaarN0 | 100% | 24 ms | 1.4 | 23.29% | 46.82% | 31.10% | 17.5 (0.7 s) |
| LBPN0_STC | 100% | 140 ms | 1.9 | 16.25% | 41.25% | 23.31% | 35.0 (1.4 s) |
| HaarN0_STC | 100% | 36 ms | 0.9 | 27.02% | 39.61% | 32.12% | 38.3 (1.5 s) |

In Table 5, it can be noticed that for all the considered videos (18), the polyp was detected in a significant number of frames, leading to a PDR of 100%. The Mean Processing Time per frame is only of 24 ms using Haar-like features without spatio-temporal coherence and of 36 ms with it, which is fully compatible with a real-time use. It is also observable that the spatio temporal coherence leads, for both local features, to an improvement of the global performances in terms of Precision and Recall as well as of F1 score. The Reaction Time also increases using spatio-temporal coherence processing with a mean delay of 1.5 s, which, nevertheless, remains compatible with a clinical use.

Table 6 shows the results obtained using both spatio-temporal coherence processing and active learning. It can be seen that the combined use of active learning strategy and spatio-temporal coherence processing leads to a significant improvement of the overall performance in terms of Precision, Recall without altering the 100% Polyp Detection Rate. HaarN1 appears to be the best local features to use with a MPT of only 21 ms and a Reaction Time of only 1.1 s.

In table 6:
N0 represents no active reinforcement;
N1 represents one active reinforcement;
N2 represents two active reinforcements;

TABLE 6

| Method | PDR | MPT | MNFP | Prec | Rec | F1 | RT |
|---|---|---|---|---|---|---|---|
| LBPN0_STC | 100% | 140 ms | 1.9 | 16.25% | 41.25% | 23.31% | 35.0 (1.4 s) |
| LBPN1_STC | 100% | 160 ms | 1.1 | 27.11% | 46.02% | 34.12% | 43.7 (1.7 s) |
| LBPN2_STC | 100% | 162 ms | 0.7 | 29.88% | 34.96% | 32.22% | 45.9 (1.8 s) |
| HaarN0_STC | 100% | 36 ms | 0.9 | 27.02% | 39.61% | 32.12% | 38.3 (1.5 s) |
| HaarN1_STC | 100% | 21 ms | 0.6 | 39.14% | 42.56% | 48.78% | 27.3 (1.1 s) |

The invention claimed is:

1. A method for performing real-time detection and displaying of polyps in optical video-colonoscopy, wherein the method comprises the steps of:
   a) acquiring and displaying a plurality of real-time images within colon regions of a video stream frame rate, each real-time image comprising a plurality of color channels;
   b) selecting only one single color channel for all the real-time images for obtaining single color pixels;
   c) scanning the single color pixels across each said real-time image with a sliding sub-window;
   d) for each position of said sliding sub-window, extracting local features from the single color pixels within the sliding sub-window of the real-time image, all the local features being only based on single-color pixels, a local feature being a function of neighboring single color pixels surrounding a given single color pixel;
   e) passing the extracted local features of single color pixels of each position of the sliding sub-window through a classifier to determine if a Region of Interest (ROI), containing a polyp, is detected for at least one series of n successive images which comprises an image $I_f$ destined to display the ROI,
   for each image of the series, spatial fusion of the sub-windows in which a same polyp is detected, for the sub-windows overlapping each other spatially on the image with at least x % of their size, to obtain $ROI_{final}$ in each successive image,
   for each series of images, temporal fusion of the $ROI_{final}$ in only one $ROI_{displayed}$, for the $ROI_{final}$ overlapping each other with at least y % of their size in the fixed referential of the images, real-time framing on display of colon regions corresponding to position of $ROI_{displayed}$ in the image $I_f$, x and y being a non-zero number, and
   the ROI being delimited by at least one sub-window generated by the sliding sub-window; and
   f) real-time framing on display of colon regions corresponding to Regions Of Interest of said sliding sub-window wherein polyps are detected.

2. The method of claim 1, wherein, for each image, the step c) of scanning is performed p times, with p being an odd number and greater than one, each time using a different size of the sliding window, the classifier is then applied to all p scans in order to decide whether a polyp is detected or not with a majority vote.

3. The method of claim 1, wherein x is greater than or equal to 50, and y is greater than or equal to 70.

4. The method of claim 2, wherein the $ROI_{displayed}$ is calculated for some series of n successive images, n being an odd number greater than or equal to 3, and a polyp is considered present in the $ROI_{final}$ if the polyp is detected at least (n+1)/2 times in the series.

5. The method of claim 1, wherein the image $I_f$ is the final image of the series.

6. The method of claim 1, wherein the time of the all the steps a), b), c), d), e), f) lasts less than 40 ms.

7. The method of claim 1, wherein the scanning of the step c) is realized without polyp boundaries detection.

8. The method of claim 1, wherein said single color channel is blue.

9. The method of claim 1, wherein local features are chosen from the group comprising local binary patterns and Haar-like features.

10. The method of claim 1, wherein each local feature is associated to a respective classifier, called weak classifier, the classifier used in step e) of the method comprising a sum of at least one hundred weak classifiers.

11. The method of claim 10, wherein the classifier is based on a boosting algorithm.

12. The method of claim 11, wherein said boosting algorithm is cascade Adaboost.

13. The method of claim 11, further comprising a preliminary step of creating said classifier by active learning.

14. The method of claim 13, wherein said active learning is carried out using a learning database or video comprising a sequence of images, wherein said images include ground truth images of known polyps, the active learning comprising the steps of:
- s1) selecting an initial set of sub-images with and without polyps, extracted from a set of said images for training, and another set of said images for testing; and selecting one single color channel from all of said images for obtaining single color pixels for the sub-images used for training and the images for testing;
- s2) extracting local features for training from the initial set of single-color sub-images used for training and local features for testing from the set of images for testing;
- s3) computing a classifier based on the boosting algorithm applied on the local features of the initial set of sub-images used for training, and testing the first classifier on the local features of the sub-set of images for testing;
- s4) for each sliding sub-window considered on the images used for testing, identifying false positive detection cases of polyps by said classifier during said testing of step s4), and creating an additional set of sub-images which present the false positive detection cases; and
- s5) using said false positive detection cases of polyps detected in the additional set of sub-images, to re-compute the classifier based on the boosting algorithm applied on the local features of the initial set of sub-images and on the local features of the additional set of sub-images,
- steps s4) to s5) being repeated a plurality of times to create a final classifier, and the classifier used in step e) of the method being said final classifier.

15. The method according to claim 1, wherein said real-time images are acquired at a minimum frame rate of 24 images per second.

16. The method of claim 1, wherein said sub-windows comprises n×m pixels, with n and m greater than or equal to 30, and wherein step d) comprises extracting at least 5 local features for each single color pixel of the sliding sub-window.

17. The method according to claim 1, wherein the plurality of real-time images forms a high-definition or a standard definition video.

18. A system for real-time image detection and displaying of polyps in optical video-colonoscopy, comprising an input port for receiving a video stream, an image processor for processing images from said video stream and an output port for outputting processed images, wherein the image processor is configured for:
- a) acquiring and displaying a plurality of real-time images within colon regions to a video stream frame rate, each real-time image comprising a plurality of color channels;
- b) selecting only one single color channel for all the real-time images for obtaining single color pixels;
- c) scanning the single color pixels across each said real-time image with a sliding sub-window;
- d) for each position of said sliding sub-window, extracting local features from the single color pixels within the sliding sub-window of the real-time image, all the local features being based only on single-color pixels from the selected single color channel selected, a local feature being a function of neighbouring single color pixels surrounding a given single color pixel;
- e) passing the extracted single color pixels local features of each sliding sub-window through a classifier to determine if a polyp is present within a region, called a Region Of Interest (ROI), for at least one series of n successive images with an image $I_f$ displaying the ROI of the sliding sub-windows,
- for each image of the series, spatial fusion of the sub-windows in which a same polyp is detected, in each successive image, for the sub-windows overlapping each other spatially on the image with at least x % of their size, to obtain $ROI_{final}$ in each successive image,
- for each series of images, temporal fusion of the $ROI_{final}$ in only one $ROI_{displayed}$, for the $ROI_{final}$ of the series overlapping each other with at least y % of their size in the fixed referential of the images, real-time framing on display of colon regions corresponding to position of $ROI_{displayed}$ in the final image $I_f$, x and y being non-zero numbers,
- the ROI being delimited by at least one sub-window generated by the sliding sub-window; and
- f) real-time framing on display of colon regions corresponding to regions of interest of said sliding sub-window wherein polyps are detected.

19. The system of claim 18, wherein the image processor is configured for realizing:
- for each image, the step c) of scanning p times, with p being an odd number and greater than one, each time using a different size of the sliding window, the classifier is then applied to all p scans in order to decide whether a polyp is detected or not with a majority vote.

20. The system of claim 18, wherein x is greater than or equal to 50, and y is greater than or equal to 70.

21. The system of claim 19, wherein the $ROI_{displayed}$ is calculated for some series of n successive images, n being an odd number greater than or equal to 3, and a polyp is considered present in the $ROI_{final}$ if the polyp is detected at least (n+1)/2 times in the series of n images.

22. An optical colonoscopy apparatus comprising a system according to claim 18, and an optical colonoscopy probe connected to an input port of said system.

* * * * *